US006251678B1

(12) United States Patent
Volkin et al.

(10) Patent No.: US 6,251,678 B1
(45) Date of Patent: Jun. 26, 2001

(54) HUMAN PAPILLOMAVIRUS VACCINE FORMULATIONS

(75) Inventors: David B. Volkin, Doylestown; Li Shi, Eagleville; Henryk Mach, Ambler, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/496,812

(22) Filed: Feb. 2, 2000

Related U.S. Application Data
(60) Provisional application No. 60/118,723, filed on Feb. 5, 1999.

(51) Int. Cl.[7] ............................. G01N 31/00; A61K 39/12
(52) U.S. Cl. ............................. 436/8; 436/18; 424/204.1; 530/350; 530/300
(58) Field of Search ........................... 424/204.1; 436/18, 436/8; 435/5; 430/493; 530/350, 300

(56) References Cited

U.S. PATENT DOCUMENTS 5,569,468 * 10/1996 Modi ................................... 424/491

FOREIGN PATENT DOCUMENTS

| | | |
|---|---|---|
| 0 659 768 A2 | 6/1995 | (EP) . |
| WO 95/10605 | 4/1995 | (WO) . |
| WO 95/31476 | 11/1995 | (WO) . |
| WO 95/31532 | 11/1995 | (WO) . |
| WO 96/30520 | 3/1996 | (WO) . |
| WO 96/15247 | 5/1996 | (WO) . |
| WO 96/29413 | 9/1996 | (WO) . |
| WO 98/34594 | 8/1998 | (WO) . |
| WO 98/44944 | 10/1998 | (WO) . |

OTHER PUBLICATIONS

Powell et al . Vaccine Design:The subunit and adjuvant approach, Pharmaceutical Biotechnology, vol. 6, pp. 205, 1995.*

Jansen et al. Vaccine, vol. 13, No. 16, pp. 1509–1514, 1995.*

Kibbe, A.H., "Polyoxyethylene Sorbitan Fatty Acid" Hand-Book of Pharmaceutical Excipients, p. 416–419, 3rd edition, 2000.

Grant, R. et al., Grant & Hackh's Chemical Dictionary, 5th Edition, 1987.

Apostolopoulos, V, et al., "Oxidative/Reductive Conjugation of Mannan to Antigen Selects for T1 or T2 Immune Responses", Proc Natl Acd Sci USA 92, pp 10128–10131, 10/95.

Breitburd, F. et al., "Immunization with VirusLike Particles from Cottontail Rabbit Papillomavirus (CRPV) Can Protect against Experimental CRPV Infection" J of Virology 69 Jun. 1995, pp. 3959–3963.

Jansen, K. et al., "Vaccination with Yeast–Expressed Cottontail Rabbit Papillomavirus (CRPV) Virus–like Particles Protects Rabbits from CPRV–induced Papilloma Formation" Vaccine 13, pp. 1 509–1514, 1995.

Powell, M. F. et al., Vaccine Design "The Subunit and Adjuvant Approach" p. 205, 1995.

Sundaram, P. et al. "Rapid, Efficient, Large–scale Purification of Unfused, Non–Denatured E7 Protein of Cottontail Rabbit Papillomavirus" Journal of Virological Methods, 57 (1996) p. 61–70.

Li, M. et al. "Expression of the Human Papillomavirus Type 11 L1 Capsid protein in *Escherichia Coli*: Characterization of Protein Domains Involved in DNA Binding and Capsid Assembly" J. Virology 71(4) 2988–2995, 1997.

Zhou, J. et al., "Identification of the Nuclear Location Signal of Human Papillomavirus Type 16 L 1 Protein" Virology 185, p. 625–635, 1991.

* cited by examiner

*Primary Examiner*—Ali R. Salimi
(74) *Attorney, Agent, or Firm*—Joanne M. Giesser; Jack L. Tribble

(57) ABSTRACT

New human papilloma virus (HPV) vaccine formulations exhibit enhanced long-term stability. Formulation components can include: virus-like particles (VLPs) absorbed onto aluminum, a salt, non-ionic surfactant, and a buffer. Additional formulations also contain a polymeric polyanionic stabilizer and a salt either in the presence or absence buffering agents and nonionic detergent.

14 Claims, 6 Drawing Sheets

HUMAN PAPILLOMAVIRUS VACCINE FORMULATIONS

This application claims priority from U.S. Provisional Patent Application No. 60/118,723 filed Feb. 5, 1999, now expired.

FIELD OF THE INVENTION

This invention related to human papillomavirus (HPV) vaccine formulations which provide enhanced long-term storage stability.

BACKGROUND OF THE INVENTION

Human Papillomavirus (HPV) infects the genital tract and has been associated with various dysplasias, cancers, and other diseases. These diseases are currently targets for vaccine development and vaccines containing virus-like particles (VLPs) which contain L1 or the combination of L1+L2 proteins are currently in clinical trials.

It has been found, however, that HPV VLPs are not stable during long-term storage, either in solution or when absorbed onto aluminum adjuvant particles.

In order to develop a commercially useful vaccine, a stable formulation is needed.

BRIEF DESCRIPTION OF THE INVENTION

This invention relates to human papillomavirus (HPV) vaccine formulations which exhibit long-term stability, the vaccines comprising: a) HPV virus-like particles (VLPs) which are adsorbed on an aluminum adjuvant; b) a salt; c) a buffer which provides for a pH range of the vaccine solution of from about pH 6.0 to about 6.5; and d) a non-ionic surfactant. In another embodiment, the formulation further comprises a polymeric polyanionic stabilizer.

Another embodiment of this invention is a vaccine comprising: a) 10–200 mcg/ml of each HPV VLP type adsorbed onto aluminum; wherein the VLPs are selected from the group consisting of: HPV 6a, HPV 6b, HPV 11, HPV 16, HPV 18, and mixtures thereof; b) 0.15 M NaCl; c) 0.05% carboxymethyl cellulose; and d) optional buffer agents and/or nonionic detergents.

This invention also relates to an improved stable vaccine formulation made by (i) adjusting the ionic strength of the solution with varying concentrations of salts; adjusting and controlling the pH of the solution with particular buffering agents; (iii) adding an non-ionic surfactant; and (iv) adding additional stabilizing excipients in the form of polymeric polyanions.

Figure 1A:
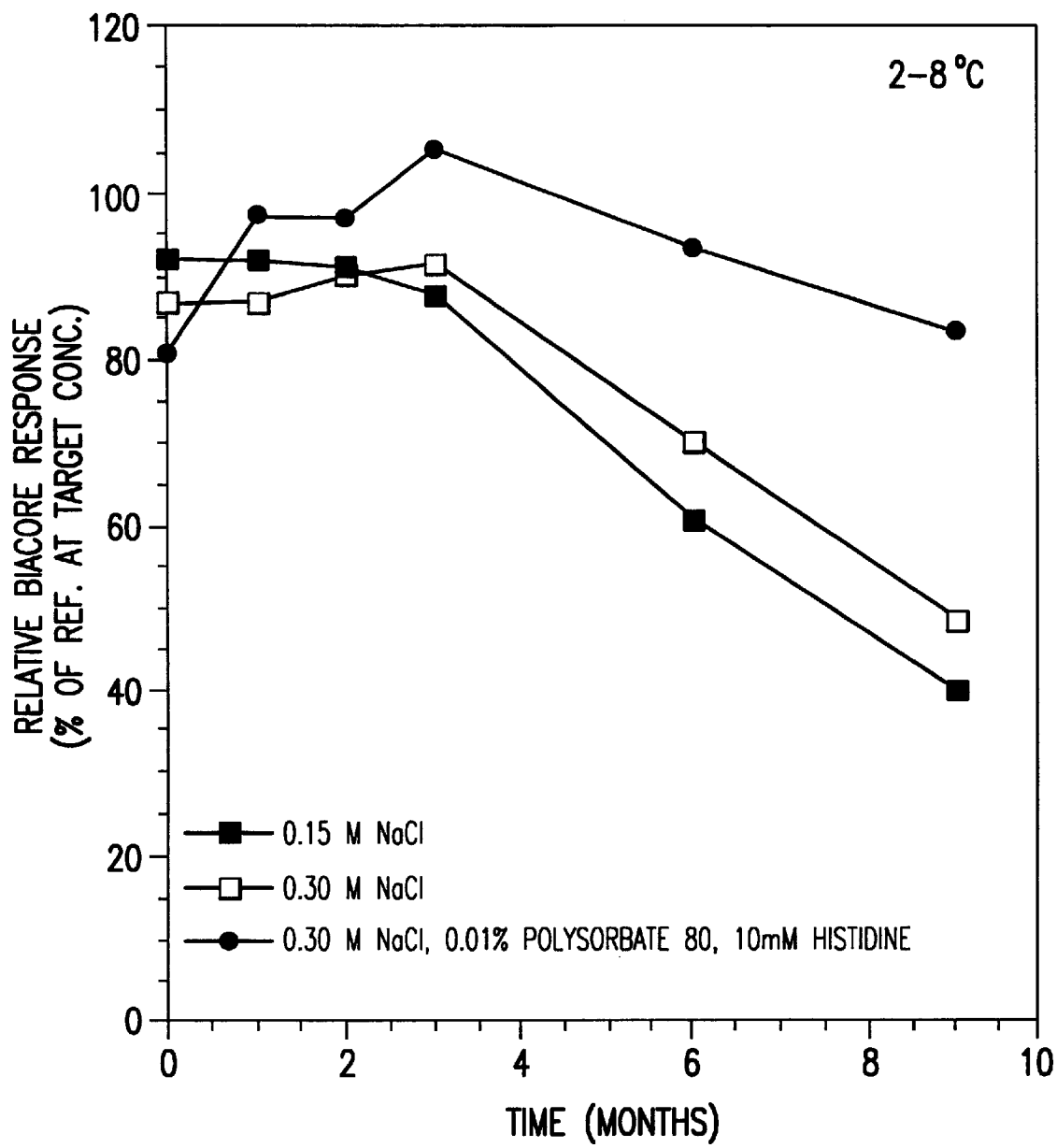
FIG. 1A is a graph showing the effects of NaCl concentration and added excipients on the stability of HPV16 VLP-aluminum formulations at 2–8° C.

Under physiological solution conditions of salt and pH, the virus like particles (VLPs) of Human Papillomavirus (HPV) L1 protein are not stable during long term storage either in solution or after adsorption to aluminum adjuvant at 2–8° C. Thus this invention relates to new formulations of both aluminum adjuvanted and non-aluminum adjuvanted HPV VLP vaccines with improved storage stability. The formulations may be in aqueous solution. In general, the HPV is absorbed onto aluminum adjuvant.

In accordance with this invention, any type of HPV VLPs may be used as the antigenic portion of the vaccine formulation. The VLPs may contain only L1 protein, or may be made of both L1 and L2 protein. The proteins may be of a wild-type amino acid composition, or they may contain mutaions. VLPs containing only L1 protein which is of a wild-type amino acid composition are preferred.

The HPVs which are particularly preferred are those associated with disease, including but not limited to: HPV 6a, HPV 6b, HPV11, HPV16, and HPV18. In addition, the formulations of this invention are suited for combinations of HPV types, including multivalent vaccines containing a plurality of HPV antigens, such as a combination of HPV 6, 11, 16 and 18. It is preferred that the VLPs be made by recombinant techniques, as is known in the art. It is particularly preferred that the host cell used to make the VLPs is a yeast cell, although other cell types, such as bacterial, insect and mammalian cells are known and currently used as hosts.

Generally, the concentration of HPV VLPs which are absorbed onto aluminum is from about 10–200 mcg/ml for each HPV VLP type. This may be adjusted, depending on such factors as antigenicity of the particular type of HPV, and the presence of multiple types of HPVs in a "cocktail"-type of vaccine.

One embodiment of this invention is a vaccine comprising a) HPV virus-like particles (VLPs) which are adsorbed on an aluminum adjuvant; b) a salt; c) a buffer which provides for a pH range of the vaccine solution of from about pH 6.0 to about 6.5; and d) a non-ionic surfactant. A further embodiment of this invention further comprises a polymeric polyanion stabilizer. Another embodiment of this invention is a formulation which omits the higher salt concentration, and comprises HPV VLPs absorbed onto aluminum, a physiological concentration of salt (about 0.15M), and a polymeric polyanionic stabilizer in the presence or absence of buffer agents and nonionic detergents.

Salts

The ionic strength of the solution is maintained by the presence of salts. Almost any salt which can contribute to the control of the ionic strength may be used. Preferred salts which can be used to adjust ionic strength are: any physiologically acceptable salt, such as NaCl, KCl, $Na_2SO_4$, $(NH_4)_2SO_4$, sodium phosphate and sodium citrate. Particularly preferred salts are: NaCl, KCl, and $Na_2SO_4$. It has been found that increasing ionic strength dramatically enhances the stability of HPV VLPs against heat induced aggregation. For example, the stability of HPV VLP protein solution was analyzed for aggregate formation as a function of temperature by using an UV spectrophotometer (turbidity assay for cloud point determination). The cloud point data indicate that increasing ionic strength (using 0.15M to 1M NaCl) dramatically enhances the stability of HPV VLPs in solution against heat-induced aggregation with the temperature of the initiation of turbidity formation being raised approximately 7° C.

The salts should be present in concentrations of from about 0.10M to 1M. However, very high concentrations are not preferred due to the practical limitations of parental injection of high salt concentrations. Instead, more moderate salt concentrations, such as more physiological concentrations of about 0.15M to about 0.5M with 0.15M–0.32M NaCl are preferred.

Buffers

Some formulations of this invention also contain a buffer to maintain the pH range so that the vaccine is in the non-irritating pH range with optimal HPV VLP stability. The effect of pH on the stability of HPVs both in solution and adsorbed to aluminum formulation were also investigated in accordance with this invention. Results indicate that HPV VLPs are stable only within a relatively small range of pH 5.5–7.0, and that the preferred pH range is 6.0–6.5, and particularly 6.2 as measured by in vitro antigenicity.

The storage stability of HPV-aluminum formulations was further tested with the addition of a buffer and non-ionic surfactant. Better pH control of the aluminum adjuvanted HPV VLP vaccine during storage was observed when either histidine or imidazole was added as a buffer agent. In general, the concentration of the buffer should range from about 2 mM to about 100 mM, with 5 mM to about 20 mM being preferred, and 10 mM being another preferred concentration. Phosphate-containing buffers are generally not preferred, as they may interact with aluminum adjuvants. The interaction of phosphate buffer ions with aluminum adjuvant as well as the non interaction of histidine and imidazole buffers with aluminum adjuvant was demonstrated by zeta potential measurements of the surface charge of the aluminum adjuvant.

Non-Ionic Surfactant

A further component in some of formulation of this invention is a non-ionic surfactant. The surfactant may be selected from the group consisting of: polyoxyethylene sorbital fatty acid esters (Polysorbates) such as Polysorbate 80 (e.g., TWEEN 80®), Polysorbate 20, (e.g., TWEEN 20®) polyoxyethylene alkyl ethers (e.g. Brij 35®, and Brij 58®), as well as others, including Triton X-100®, Triton X-114®, NP-40®, Span 85 and the Pluronic series of non-ionic surfactants (e.g. Pluronic 121), with Polysorbate 80 being particularly preferred. The surfactant is generally present in a concentration of from about 0.0005% to about 0.5% (wt/vol). Polysorbate 80 was found to protect HPV VLP-aluminum from inactivation during simulated shipping stress (i.e., shaking or stirring). For Polysorbate 80, a preferred concentration is about 0.01%.

Polymeric Polyanion Stabilizer

A further significant enhancement of the stability of the HPV-VLP formulation may also accomplished by the addition of polyanionic, polymeric excipients, such as a stabilizer. As used throughout the specification and claims, the term "polyanionic polymer" is meant to refer to compounds which have either a single long chain, or those with multiple cross linked chains; either type possessing multiple negative charges along the chain(s) when in solution. Examples of polyanionic polymers include: proteins, polyanions, peptides and poly-nucleic acids. Specific stabilizers may be selected from the group consisting of:

carboxymethyl cellulose (particularly 10–800 cps),
heparin (6–30 kDa),
poly-amino acids (2–100 kDa) such as poly(Glu), Poly (Asp), and Poly(Glu, Phe),
oxidized glutathione [Glu-Cys-Gly]$_2$ (613 Da),
poly-nucleotides such as polycytidylic acid (200–700 kDa), and polyadenylic acid (200–700 kDa),
RNA,
DNA, and
serum albumins.

The concentration of the stabilizer, when present, is from about 0.01% to about 0.5%, particularly about 0.05–0.1% (by weight), although the addition of even a ten fold lower amount of polyanionic excipients (for example, 0.01% albumin, DNA or heparin) still provides enhanced stability to HPV VLP-aluminum formulations, although the stabilizing effect is relatively less significant perhaps due to the lower concentrations. As described in more detail in the Examples, polyanions provided a dramatic stabilization of HPV-aluminum formulations. The stabilizing mechanisms of these classes of excipients may vary from directly binding to HPV VLP molecule (such as occurs with DNA), inhibiting HPV VLP or HPV VLP-aluminum adsorption on surfaces, increasing solution viscosity, neutralizing surface charge, reformation of HPV VLP disulfide bonds or interfering with amino acid side chain oxidation, and/or increasing the conformational rigidity of HPV VLPs. It is important to note that HPV VLP L1 protein contains a polyanion binding site of multiple positively charged amino acids in the C-terminal region of the protein.

These polyanions were further tested under accelerated stability study conditions at 37° C. Polyanion containing formulations of HPV-aluminum retained about 80% of in vitro antigenicity while the control HPV formulation (without addition of polyanions) had almost no in vitro antigenicity after one week of incubation at 37° C. The same set of samples after two weeks of incubation at 37° C. show no significant difference from the one-week data indicating the strong stabilizing effect of these polyanionic excipients.

The polyanion stabilization effect was also investigated for HPV VLPs in solution under accelerated conditions at 37° C. The data indicate that for polynucleotide polyanions, poly(A) or poly(C), a concentration of 0.001% (by weight or 10 mcg/ml) is required for HPV16 VLP (at 80 mcg/ml protein) to maintain maximum stability against heat induced inactivation as measured by in vitro antigenicity. Sedimentation and UV analysis indicates that polyanions bind to the VLP directly.

In addition, HPV VLP adsorption to aluminum adjuvant may be inhibited by prebinding of polyanions to the HPV VLP. For example, carboxymethyl cellulose can inhibit HPV VLP binding to aluminum at certain concentrations of the polyanion. The addition of carboxymethyl cellulose after HPV VLP adsorption to aluminum adjuvant, however, results in virtually no detectable release of HPV VLP from aluminum while providing a dramatic stability enhancement in a concentration dependent manner.

Especially preferred among the polyanions (0.001–0.25% by weight) is carboxymethyl cellulose, (10–800 cps) with an approximate typical molecular weight of 50,000–700,000 Da, with lower viscosity 10–200 cps carboxymethyl cellulose being especially preferred.

Preferred formulations of this invention include the following:

I. a) 10–200 mcg/ml of each HPV VLP type absorbed onto aluminum, wherein the VLPs are selected from the group consisting of: HPV 6a, HPV 6b, HPV 11, HPV 16, HPV 18, and mixtures thereof; b) 0.32 M NaCl; c) 10 mM histidine buffer, pH 6.2; and d) 0.01% Polysorbate 80.

II. a) 10–200 mcg/ml of each HPV VLP type absorbed onto aluminum, wherein the VLPs are selected from the group consisting of: HPV 6a, HPV 6b, HPV 11, HPV 16, HPV 18, and mixtures thereof; b) 0.32 M NaCl; c) 10 mM histidine buffer, pH 6.2; d) 0.01% Polysorbate 80, and 0.05% carboxymethyl cellulose.

III. a) 10–200 mcg/ml of each HPV VLP type adsorbed onto aluminum, wherein the VLPs are selected from the group consisting of: HPV 6a, HPV 6b, HPV 11, HPV 16, HPV 18, and mixtures thereof; b) 0.15 M NaCl; and c) 0.05% carboxymethyl cellulose; and d) optionally 10 mM histidine, pH 6.2 and 0.01% polysorbate 80.

The following non-limiting Examples are presented to better illustrate the invention.

EXAMPLE 1

General Methods

A frozen solution of yeast derived recombinant L1 protein HPV16 VLP (with greater than 95% purity) at a protein concentration of 870 mcg/ml in 0.5M NaCl, 0.003% polysorbate 80, pH of approximately 6.2 was used for most of these experiments. Aluminum adjuvant was manufactured at Merck. Excipients were purchased commercially. All the vaccine formulations were prepared as follows: The HPV VLP solution with or without dilution was added to aluminum adjuvant for HPV VLP alum adsorption, then the excipients were added. All final desired concentrations for all excipients, HPV VLP and aluminum adjuvant in the formulation could be approached by either direct mixing with designed volume, or by adjusting with a settle/decant process.

In vitro Antigenicity Assays.

To release HPV from the aluminum adjuvant, an aluminum dissolution method was developed which included dilution of HPV-aluminum formulation into a high salt solution containing citrate and polysorbate 80. The HPV VLP samples from the aluminum dissolution method are directly subjected to an in vitro antigenicity assay using Biacore analysis (utilizing an HPV VLP type specific neutralizing antibody). The HPV VLPs samples from the aluminum adjuvanted stability studies are directly compared to a frozen stock solution of the same HPV VLP to determine in vitro antigenicity.

pH Measurement.

The pH measurements of HPV-aluminum formulations were performed at ambient temperature using an Orion pH meter of model 420A. All samples incubated at various temperatures were equilibrated at room temperature for 30 minutes before pH determination. The pH meter was calibrated manually using two standard buffers that bracket the expected sample pH range, with a correlation coefficient between 95%–100%. Temperature effect on the pH of histidine buffered solutions was determined by varying temperature gradually from 4° C. to 37° C.

Protein Concentration Determination (UV Spectroscopy)

The protein concentration of HPV in both bulk solutions andformulated samples (after aluminum dissolution) were determined by UV absorbance spectra measurement at ambient temperature using a HP 8452A Diode Array spectrophotometer and a cuvette with a path length of 1 cm. The sample volumes used were approximately 200 to 250 microliters. The protein concentration was calculated using a multicomponent second derivative analysis technique developed for use with HPV VLPs.

Other Analyses

Sedimentation velocity experiments were performed using Beckman XL1 analytical ultracentrifuge.

Turbidity assays were carried out using a HP 8452A Diode Array spectrophotometer equipped with a HP 845X UV-Visible system software and a temperature control system. The light scattering of the solutions were followed at 320–350 nm under the kinetic mode of the program by increasing the temperature from about 25° C. to 80° C.

Zeta potential of aluminum particles and HPV VLPs were determined using a Malvern Zetasizer 3000 System with varying the solution pH from 4 to 9 or the excipient concentrations.

Accelerated and Real Time Stability Studies.

HPV-aluminum formulation stability studies were carried out under both accelerated and real time conditions. The temperature of accelerated stability studies varied from 15° C. to 37° C. The temperature of real time stability studies was at 2–8° C. These temperature ranges were chosen based on the fact that HPV VLP inactivation rate is very sensitive to temperature. Previous conformational integrity data via biophysicalmeasurements have shown that increasing the temperature to above 40–45° C. induces significant conformational changes in the HPV VLP in solution, a condition which needs to be avoided in accelerated stability studies.

EXAMPLE 2

Effects of Salt and Excipients on Stability

Figure 1B:
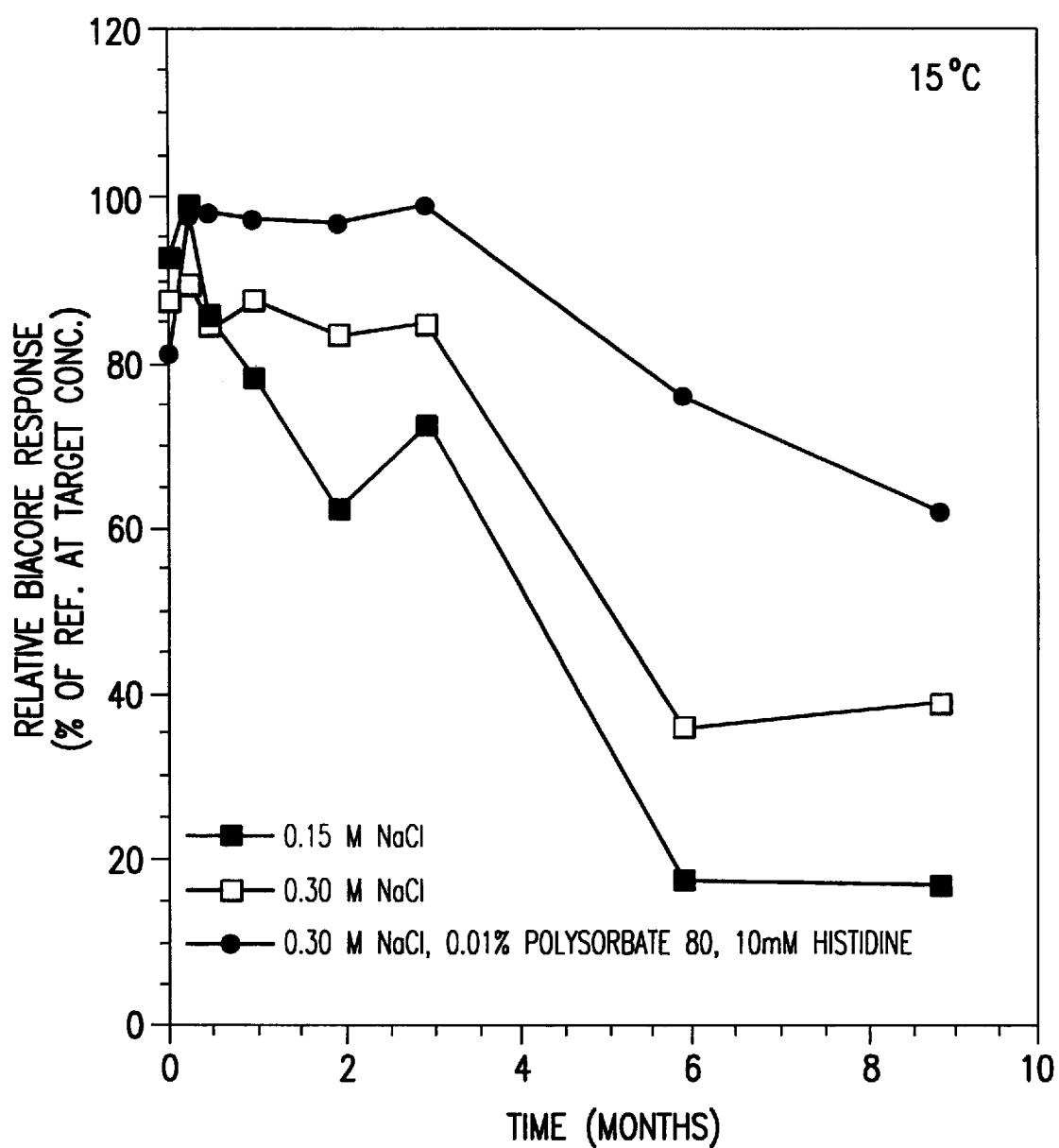
FIG. 1B shows the results at 15° C.

The effects of NaCl concentration and added excipients on the stability of HPV16 VLP-aluminum formulations at 2–8° C. was investigated. Formulations of 160 mcg/ml HPV16 VLP on 450 mcg/ml aluminum adjuvant in different NaCl concentration solution with/without the addition of 0.01% Polysorbate 80, 10 mM histidine were incubated at 2–8° C. The in vitro antigenicity of the formulations was then assayed after different incubation times by Biacore analysis. Results are shown in FIG. 1A. The experiment was then repeated for incubation at 15° C. FIG. 1B shows the results when incubated at 15° C. In both graphs, closed squares are the points for 0.15M NaCl; open squares are the points for 0.30M NaCl; closed circles are for 0.30 M NaCl, 0.01% Polysorbate 80, and 10 mM histidine. The data indicate that increasing salt concentration enhances the vaccine stability and the addition of buffer and polysorbate further enhances the stability.

EXAMPLE 3

Effects of Stabilizers

Figure 2:
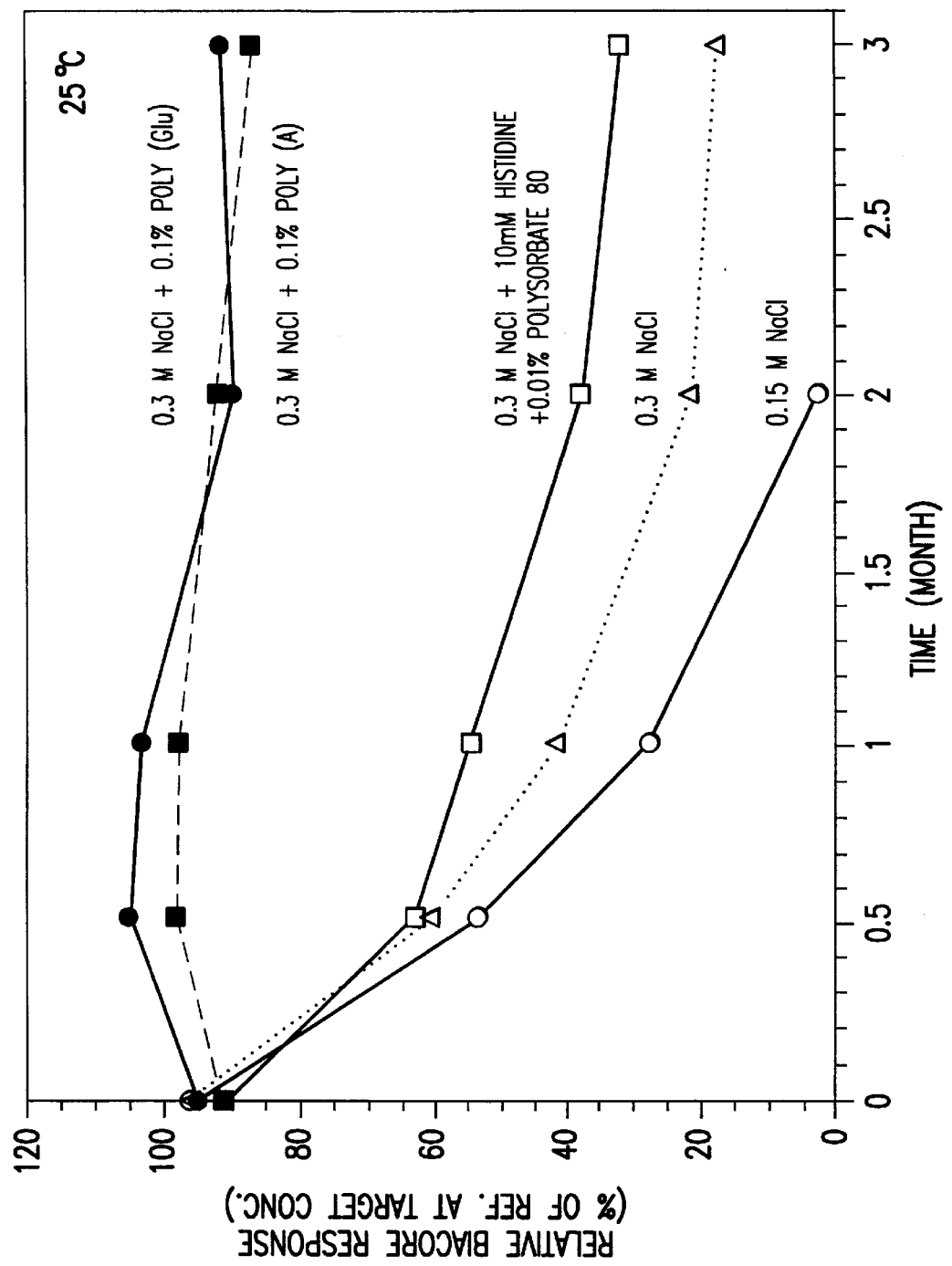
FIG. 2 is a graph showing the effects of excipients on the accelerated stability of HPV16 VLP-aluminum formulations.

The effects of stabilizing excipients on the accelerated stability of HPV16 VLP-aluminum formulations was investigated. Formulations of 200 mcg/ml HPV16 VLP on 450 mcg/ml aluminum adjuvant with/without the addition of different stabilizing excipients were incubated at pH 6.2 and 25° C. The in vitro antigenicity of the formulations was then assayed after different incubation times by Biacore analysis. The formulation compositions are shown in FIG. 2: closed circles are for 0.3M NaCl+0.1% polyglutamic acid (poly-Glu); crossed squares are for 0.3M NaCl+0.1% polyadenylic acid (poly-A); open squares are for 0.3M NaCl+10 mM histidine+0.01% polysorbate 80; open triangles are for 0.3M NaCl; and open circles are for 0.15M NaCl. The data indicate that at 25° C., increasing salt concentration from 0.15 to 0.3 M and adding buffer and polysorbate enhances the stability of the formulation. The addition of a polyanion, however, more dramatically enhances the stability of aluminum adsorbed HPV VLPs against heat induced loss of in vitro antigenicity.

EXAMPLE 4

Effects of Polyanions on Stability

Figure 3:
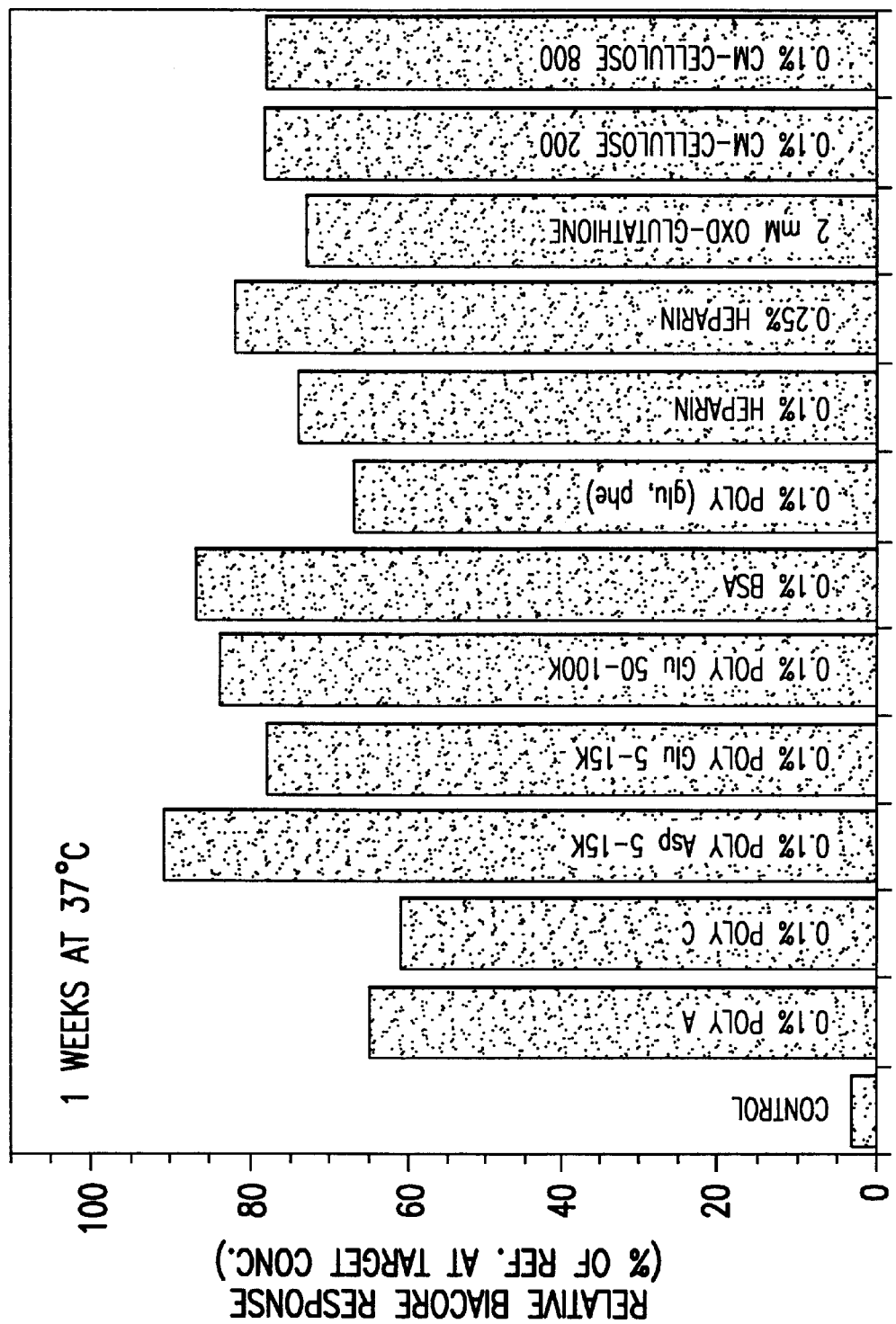
FIG. 3 is a bar graph showing the effects of polyanion excipients on the accelerated stability of HPV16 VLP-aluminum formulations.

The effects of polyanion excipients on the accelerated stability of HPV16 VLP-aluminum formulations was investigated in more detail. Formulations of 160 mcg/ml HPV16 VLP on 450 mcg/ml aluminum adjuvant in 0.3 M NaCl, 0.01% Polysorbate 80, 10 mM Histidine, pH 6.2 with/without the addition of a polyanion excipient were incubated at 37° C. for 1 week. The in vitro antigenicity of the formulations was then assayed by Biacore analysis. The kinds and concentrations of polyanion excipients added are as shown in FIG. 3, from left to right: control; 0.1% poly Adenylic acid (Poly A); 0.1% poly Cytidylic acid (poly C); 0.1% poly Aspartic acid (poly Asp) (5–15K); 0.1% poly Glutamic acid (poly-Glu) (5–15K); 0.1% poly Glutamic acid (poly-Glu) (50–100K); 0.1% bovine serum albumin (BSA); 0.1% poly Glutamic acid-Phenylalanine (poly Glu, Phe); 0.1% heparin; 0.25% heparin; 2 mM oxidized-Glutathione; 0.1% carboxymethylcellulose (CMC) (200 cps); 0.1% carboxymethyl cellulose (CMC) (800 cps).

It can be seen that all these polymeric polyanions have the ability to significantly stabilize BPV16 VLP-aluminum formulations as seen by the maintenance of in vitro antigenicity as measured by Biacore.

EXAMPLE 5
The Effect of Carboxymethyl Cellulose

Figure 4:
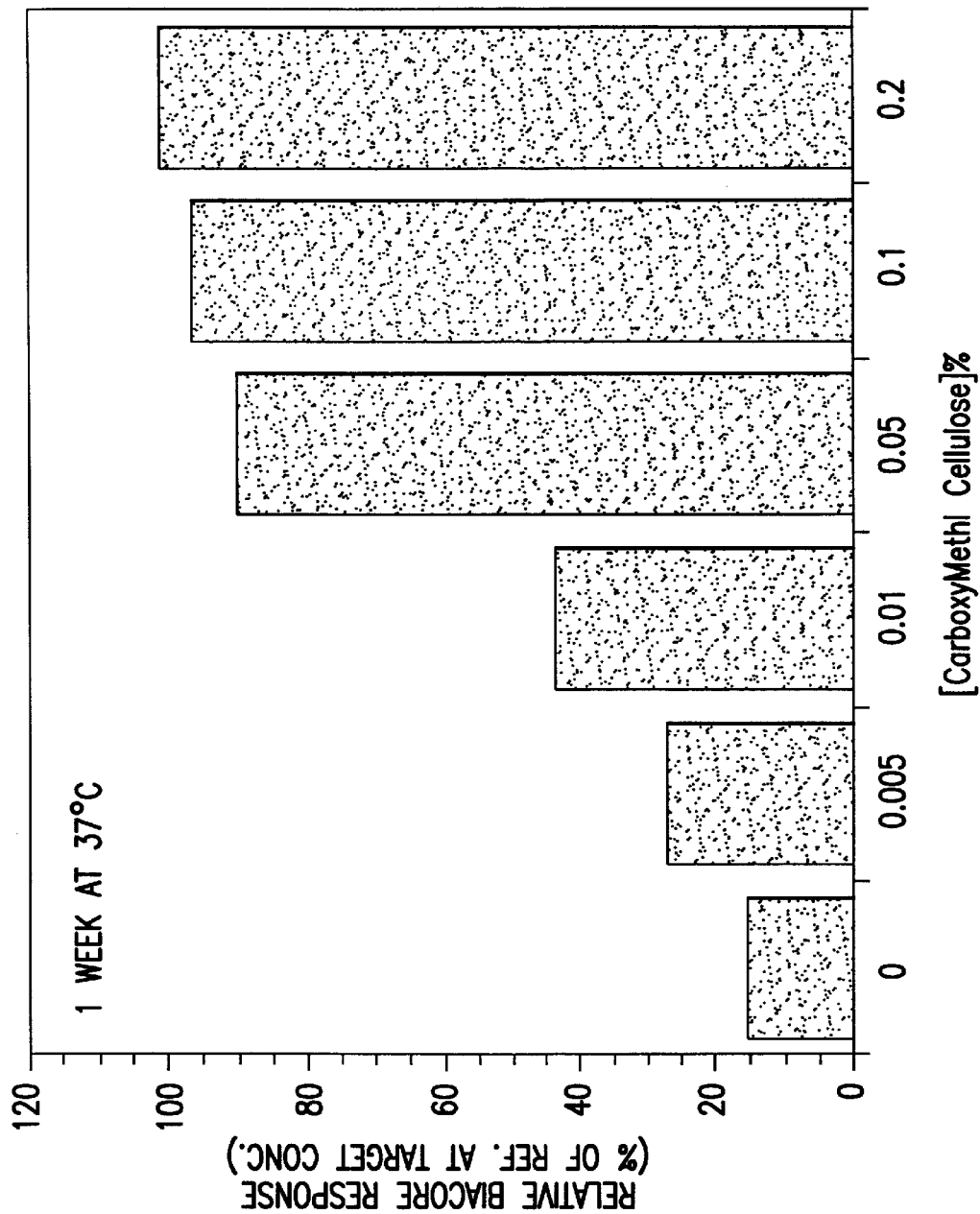
FIG. 4 is a bar graph illustrating the effect of carboxymethyl cellulose (CMC) concentration on the accelerated stability of HPV16VLP-aluminum formulations.

The effect of carboxymethyl cellulose (CMC) concentration on the accelerated stability of HPV16 VLP-aluminum formulations was examined. Formulations of 160 mcg/ml HPV16 on 450 mcg/ml aluminum adjuvant in 0.3 M NaCl, 0.01% polysorbate 80, 10 mM Histidine, pH 6.2 with/without the addition of different amount of CMC (200 cps) were incubated at 37° C. for 1 week. The in vitro antigenicity of the formulations was then assayed by Biacore analysis. Results are shown in FIG. 4 for 0, 0.005%, 0.01%, 0.05%, 0.1% and 0.2% CMC. The data indicate that the stability enhancement is a function of added CMC concentration. In vitro antigenicity is retained in the presence of at least 0.05% CMC.

EXAMPLE 6
Effects of Size of CMC

Figure 5:
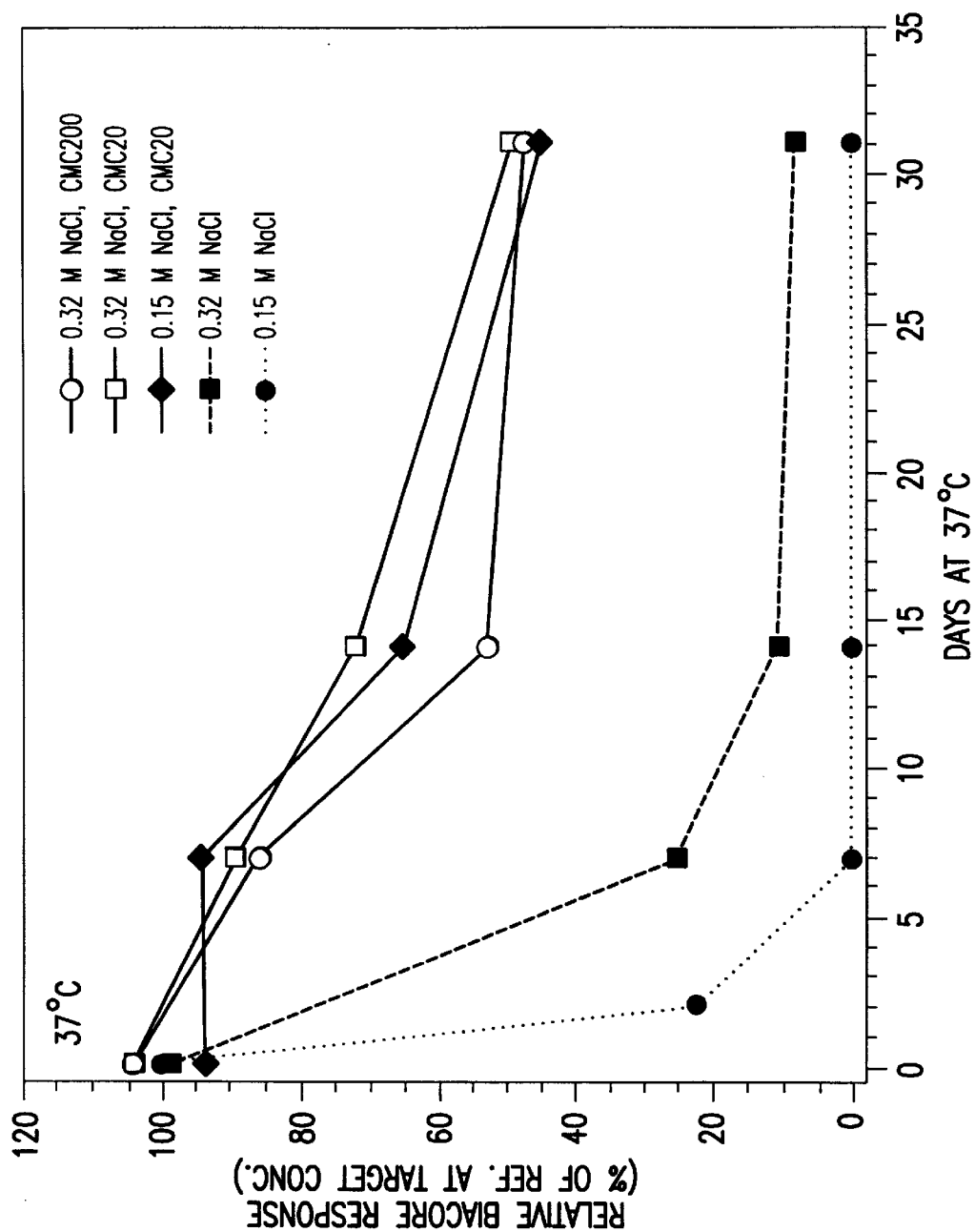
FIG. 5 is a graph showing the effects of carboxymethyl cellulose (CMC) molecular weight and NaCl concentration on the accelerated stability of HPV16 VLP-aluminum formulations.

The effects of carboxymethyl cellulose (CMC) molecular weight and NaCl concentration on the accelerated stability of HPV16 VLP-aluminum formulations was examined. Formulations of 160 mcg/ml HPV16 VLP on 450 mcg/ml aluminum adjuvant in 10 mM Histidine, pH 6.2, 0.01% polysorbate 80 with/without the addition of CMC were incubated at 37° C. The in vitro antigenicity of the formulations was then assayed after different incubation times by Biacore analysis. The CMC concentrations was 0.05%, and the CMC molecular weight is either 10–20 cps or 200 cps level. Results are given in FIG. 5: open circle is for 0.32M NaCl, CMC 200 cps; open square with solid line is for 0.32 M NaCl, CMC 10–20 cps; closed diamond is for 0.15M NaCl, CMC 10–20 cps; open square with dotted line is for 0.32 M NaCl; and closed circle is for 0.15M NaCl. The data indicate the CMC with smaller molecular weight (about 10–20 cps) basically provides similar stability enhancement to HPV VLP-aluminum formulations with CMC 200 cps and that the presence of CMC allows the vaccine preparation to be formulated at a physiological salt concentration (0.15 M NaCl).

What is claimed is:

1. A human papillomavirus (HPV) vaccine formulation comprising:
    a) 10–200 mcg/ml of each HPV virus-like particle (VLP) type adsorbed onto aluminum, wherein the VLPs are selected from the group consisting of: HPV 6a, HPV 6b, HPV 11, HPV 16, HPV 18, and mixtures thereof;
    b) a physiologically acceptable salt selected from the group consisting of: NaCl, KCl, $Na_2SO_4$, $(NH_4)_2SO_4$, sodium phosphate and sodium citrate;
    c) a histidine buffer which provides for a pH range of the vaccine solution of from about pH 6.0 to about 6.5; and
    d) a non-ionic surfactant selected from the group consisting of: polyoxyethylene sorbitol fatty acid esters, polyoxyethylene alkyl esters, TRITON X-100®, TRITON X-114®, NP-40®, Span 85, and the Pluronic series of non-ionic surfactants.

2. A vaccine according to claim 1 wherein the salt is present in a concentration of from about 0.10M to about 0.5M.

3. A vaccine according to claim 2 wherein the salt is 0.32M NaCl.

4. A vaccine according to claim 1 wherein the buffer is present is a concentration of about 2 mM to about 100 mM.

5. An HPV vaccine according to claim 1 wherein the surfactant is present in a concentration of from about 0.0005% to about 0.5% (wt/vol).

6. A vaccine according to claim 1 which is in a aqueous solution.

7. A vaccine formulation according to claim 1 comprising:
    a) 10–200 mcg/ml of each HPV virus-like particle (VLP) type adsorbed onto aluminum, wherein the VLPs are selected from the group consisting of: HPV 6a, HPV 6b, HPV 11, HPV 16, HPV 18, and mixtures thereof;
    b) 0.32M NaCl;
    c) 10 mM histidine buffer which provides for a pH of 6.2; and
    d) 0.01% Polysorbate 80.

8. A vaccine according to claim 1 further comprising a polymeric polyanionic stabilizer.

9. A vaccine according to claim 8 wherein the stabilizer is selected from the group consisting of: carboxymethyl cellulose (CMC), heparin, Poly(Glu), Poly(Asp), Poly(Glu, Phe), oxidized glutathione, polycytidylic acid, polyadenylic acid, RNA, DNA, and serum albumins.

10. A vaccine according to claim 9 wherein the stabilizer is CMC.

11. A vaccine according to claim 8 wherein the concentration of the stabilizer is from about 0.01% to about 0.5% (by weight/volume).

12. An HPV vaccine formulation comprising:
    a) 10–200 mcg/ml of each HPV virus-like particle (VLP) type adsorbed onto aluminum, wherein the VLPs are selected from the group consisting of: HPV 6a, HPV 6b, HPV 11, HPV 16, HPV 18, and mixtures thereof;
    b) 0.32M NaCl;
    c) 10 mM histidine buffer which provides for a pH of 6.2;
    d) 0.01% Polysorbate 80; and
    e) 0.05% CMC.

13. An HPV vaccine formulation comprising:
    a) 10–200 mcg/ml of each HPV virus-like particle (VLP) type adsorbed onto aluminum, wherein the VLPs are selected from the group consisting of: HPV 6a, HPV 6b, HPV 11, HPV 16, HPV 18, and mixtures thereof;
    b) 0.15M NaCl;
    c) 0.05% CMC; and
    d) an optional buffer which provides for a pH range of the vaccine solution of from about pH 6.0 to about 6.9 and/or non-ionic detergent.

14. A vaccine according to claim 12 which is in an aqueous solution.

* * * * *